US006413205B1

(12) United States Patent
Finny

(10) Patent No.: US 6,413,205 B1

(45) Date of Patent: Jul. 2, 2002

(54) INFANT WARMER WITH LIGHT SHIELD

(75) Inventor: Rosamma K. Finny, Missouri City, TX (US)

(73) Assignee: Harris County Hospital District, Houston, TX (US)

(*) Notice: Subject to any disclaimer, the term of this patent is extended or adjusted under 35 U.S.C. 154(b) by 21 days.

(21) Appl. No.: 09/663,233

(22) Filed: Sep. 15, 2000

Related U.S. Application Data

(60) Provisional application No. 60/205,349, filed on May 18, 2000.

(51) Int. Cl.[7] .......................... A61G 11/00; A61N 5/00; F26B 3/30

(52) U.S. Cl. ............................ 600/22; 607/91; 392/418

(58) Field of Search ............................ 600/22; 607/91; 392/439, 418; 296/97.21

(56) References Cited

U.S. PATENT DOCUMENTS 1,900,342 A * 3/1933 Hess ........................... 600/22
3,799,606 A * 3/1974 Gesslein .................. 296/97.21
3,822,706 A * 7/1974 Simone et al. ................ 607/94
4,617,912 A 10/1986 Beer et al. .................. 128/1 B
5,285,519 A * 2/1994 Barsky et al. .............. 392/439
5,474,517 A 12/1995 Falk et al. .................... 600/22
5,498,229 A 3/1996 Barsky et al. ................ 600/22
5,649,896 A 7/1997 Barsky ........................ 600/22
5,841,944 A 11/1998 Hutchinson et al. ........ 392/418
5,898,817 A 4/1999 Salmon et al. .............. 392/418
5,915,072 A * 6/1999 Campbell et al. ........... 392/418
5,980,449 A 11/1999 Benson et al. ................ 600/22

OTHER PUBLICATIONS

Ferragno and Storia, "The History of Incubators," 27 pages, on the Internet at http://members.spree.com/sip/terragno/storia.htm as of May 10, 2000. No admission that this is prior art.

Gray, Dostal, Ternullo–Retta and Armstrong, "Developmentally Supportive Care in a Neonatal Intensive Care Unit: a Research Utilization Project." Neonatal Network, vol. 17, No. 2, pp. 33–38, Mar., 1998.

* cited by examiner

*Primary Examiner*—Eric F. Winakur
*Assistant Examiner*—Nikita R. Veniaminov
(74) *Attorney, Agent, or Firm*—Vinson & Elkins L.L.P.

(57) ABSTRACT

An infant warmer has a bed assembly for supporting a baby born prematurely and a heat source with controls capable of maintaining the infant's body temperature within a desired range. The bed assembly is suitably supported to hold the infant at a convenient elevation. A light shield rests on the bed assembly and is adapted to block light from directly entering the eyes of the infant.

14 Claims, 1 Drawing Sheet

INFANT WARMER WITH LIGHT SHIELD

CROSS-REFERENCE TO RELATED APPLICATION

Priority is claimed to U.S. Provisional Patent Application Serial No. 60/205,349 filed on May 18, 2000, which is incorporated by reference.

BACKGROUND OF THE INVENTION

This invention pertains to infant warmers, and more particularly to an infant warmer having a shield adapted for protecting an infant's eyes from light. Infant warmers are used for hospital care of newborn babies, particularly those born prematurely and having a low birth weight. Infant warmers typically have a bed for receiving and supporting the newborn baby with a heat source, such as a radiant heater, located above the bed. The heater is thermostatically controlled to maintain the infant's body temperature within a desired range. U.S. Pat. Nos. 5,498,229; 5,841,944; and 5,898,817, issued to Barsky et al., Hutchinson et al., and Salmon et al., respectively, provide examples of prior art infant warmers.

SUMMARY OF THE INVENTION

An infant warmer is provided that has a bed support holding an infant bed assembly, which is adapted for supporting an infant, such as a baby born prematurely with a low birth weight. A heat source is located above the bed assembly and is held by a support structure that is attached to the bed assembly or to the bed support. A light shield is located on a portion of the bed assembly. The light shield is preferably transparent and capable of supporting an opaque material so that light from a source above the infant is blocked from directly entering the infant's eyes.

The infant warmer preferably includes a light source that is useful to medical personnel examining the infant, and the light shield is preferably adapted to prevent light from the examining light from entering the infant's eyes directly. The bed assembly has a length, and the light shield preferably covers less than about 50 percent of the length. The light shield is preferably made of a substantially rigid material, and the light shield preferably removably rests upon the bed assembly.

In another aspect, the present invention provides a light shield that is adapted to rest on a bed assembly of an infant warmer. The light shield comprises a sheet of substantially rigid material that is formed to provide a lower support surface, which is adapted to contact the bed assembly of the infant warmer. The lower support surface rests on the bed assembly, and the sheet is formed to extend above and over the bed assembly. Sufficient space is provided between an inside upper surface of the sheet and an upper surface of the bed assembly so that the infant's head can rest on the upper surface of the bed assembly and be spaced apart from the inside upper surface of the sheet of substantially rigid material. The sheet of substantially rigid material is preferably further adapted to block a substantial portion of light from passing through the sheet of substantially rigid material.

BRIEF DESCRIPTION OF THE DRAWINGS

The summary of the invention, as well as the following detailed description of preferred embodiments of the invention, will be better understood when read in conjunction with the appended drawings. Embodiments of the invention are illustrated in the drawings for the purpose of explaining the invention, but the invention is not limited to the illustrated embodiments. In the drawings.

DETAILED DESCRIPTION OF THE INVENTION

Infant warmers are typically located in a neonatal unit of a hospital, and the neonatal unit typically has ceiling lights. Further, an infant warmer may have a light that is used when medical personnel examine a baby. Lights such as these shine into the eyes of the baby in the infant warmer and is believed to be an undesirable stimulus for the baby.

Figure 1:
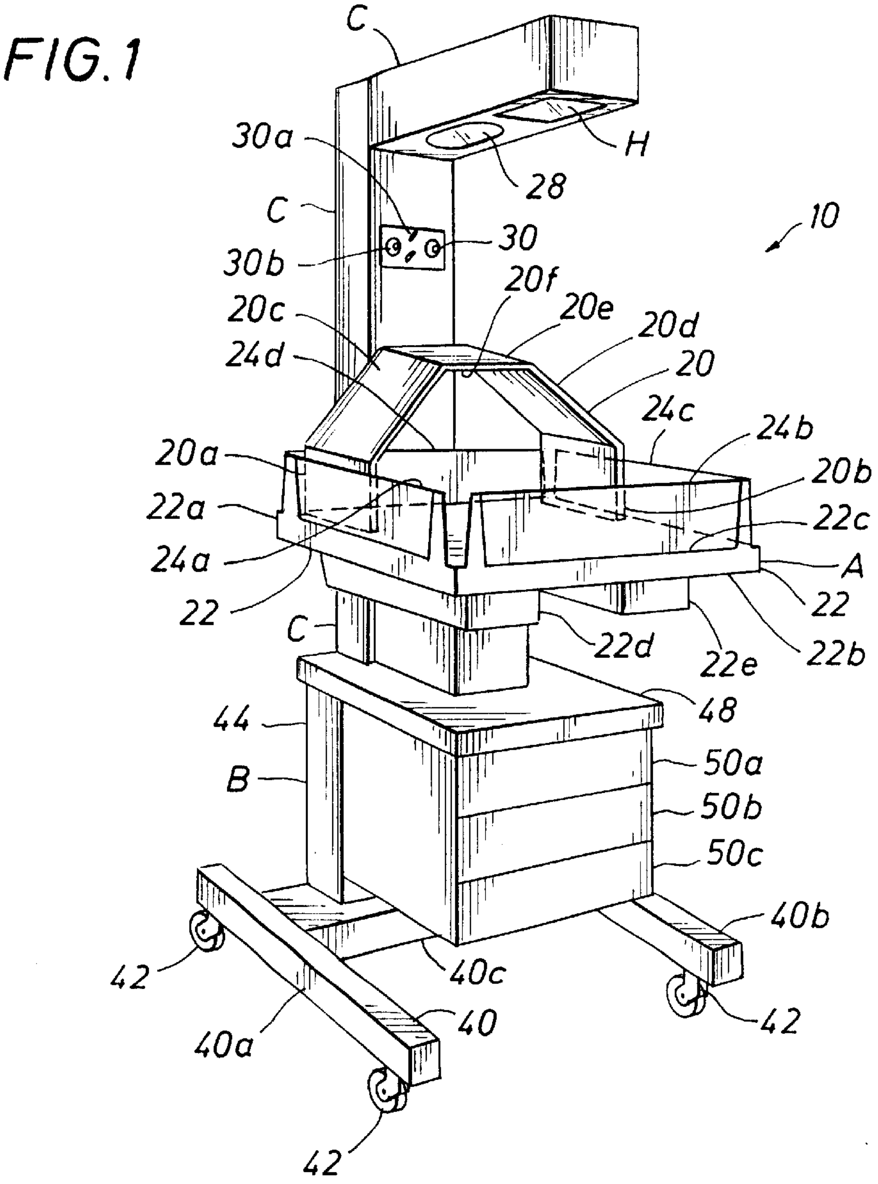
FIG. 1 is a perspective view of an infant warmer according to the present invention.

With reference to FIG. 1, an infant heater 10 is illustrated according to the present invention. Infant heater 10 has a bed assembly A, a bed support B that holds and supports bed assembly A, and a support structure C, which holds a heat source H. A light shield 20 rests on bed assembly A, and light shield 20 can be adapted to reduce the amount of light that enters the eyes of a baby positioned below the light shield, thus protecting the baby from an undesirable stimulation.

Bed assembly A includes a bed 22, which has a head end 22*a* and a foot end 22*b*. Light shield 20 rests on or in bed 22 at head end 22*a*. Bed 22 has an upper surface 22*c*, and a newborn infant, such as a baby born prematurely and having a low birth weight, would be placed on upper surface 22*a*. The infant's head would be placed towards head end 22*a*, and the infant's feet would be placed towards foot end 22B. Bed assembly A includes side panels 24*a*, 24*b*, 24*c* and 24*d*. Side panels 24 (suffixes omitted for simplicity) help to hold heat within bed assembly A so that an infant resting on bed 22 will stay warmer. The infant is typically approximately centered between side panels 24*a* and 24*c*.

Light shield 20 is adapted to cover the head of the infant. In one embodiment, light shield 20 is made of a transparent plastic material such as an acrylic material. In this embodiment, an opaque blanket can be placed over light shield 20 to block a substantial portion of light from entering directly into the infant's eyes. Infant heater 10 has a light 28 held by support structure C. Light 28 is generally left off, but turned on by a medical person using a switch 30*a* in a control panel 30. The medical person may activate light 28 by moving switch 30*a* when examining the infant. The light from light 28 is believed to be an uncomfortable stimulation for the infant, so light shield 20 is preferably used when light 28 is on.

Light shield 20 may be used at any time, such as when ceiling lights are on, which light would travel into the eyes of the infant in infant heater 10, except when light shield 20 is used to block the light. Light shield 20 can have various configurations and can be made of various materials. Light shield 20 is illustrated in FIG. 1 as having opposing vertical sides 20*a* and 20*b*, each of which has a lower surface for contacting bed assembly A and holding light shield 20 in a stable position. Extending from vertical members 20*a* and 20*b*, light shield 20 has angled members 20*c* and 20*d* that angle inwardly towards each other and above vertical members 20*a* and 20*b*. Light shield 20 has an upper planar member 20*e*, which is typically in an approximately horizontal plane while in use. Angled members 20*c* and 20*d* join with and support planar member 20*e*, holding planar member 20*e* above upper surface 22*c* of bed 22.

Planar member 20*e* has an inside upper surface 20*f* that is sufficiently spaced from upper surface 22*c* of bed 22 to accommodate the infant's head. For example, vertical members 20*a* and 20*b* may extend upwardly a distance equivalent to the diameter of the infant's head, or up to about two or three times that diameter, and angled members 20*c* and 20*d* may extend upwardly and inwardly so as to hold planar member 20*e* at a distance spaced from the infant's eyes.

Light shield 20 may be opaque and may be made of a metal or opaque plastic material, or it may be made of wood. In one embodiment, light shield 20 is made of a substantially transparent material, such as an acrylic material, and light shield 20 is covered by an opaque material, such as a baby blanket. Any suitable opaque material can be used to cover light shield 20 so as to make it substantially impervious to light rays. Light shield 20 can also be made of a thermally insulating material so as to help keep the infant warm by partially preventing heat loss from the infant's head. In another embodiment, the light shield can be a frame for holding an opaque material, such as a blanket, and the frame may have no solid planar members. Such a frame can be made of wire.

Bed 22 has a length between head end 22*a* and foot end 22*b*. Light shield 20 is located toward head end 22*a* and extends toward foot end 22*b*. Light shield 20 preferably covers enough of bed 22 so as to substantially block light from directly entering the infant's eyes. At the same time, it is believed that a portion of upper surface 22*c* should not be covered so as to provide access to the infant by medical personnel and/or to allow heat from heat source H to pass directly to the infant or upper surface 22*c* of bed 22. In one embodiment light shield 20 covers up to about 60 percent of the length of bed 22. In other embodiments, light shield 20 covers between 10 and 50 percent of the length of bed 22, 20 to 40 percent of the length of bed 22, 15 to 35 percent of the length of bed assembly 22, or about 25 percent of the length of bed 22.

With continued reference to FIG. 1, bed support B of infant heater 10 includes a frame 40, which has rails 40*a* and 40*b* connected together by a cross member 40*c*. Wheels or casters 42 are attached to frame 40, which allow infant heater 10 to be rolled easily on a floor. A support column 44 extends upwardly from cross member 40*c* of frame 40. Support structure C is secured to support column 44. In the embodiment illustrated in FIG. 1, support structure C extends upwardly from support column 44, and bed assembly A is secured to support structure C, but other arrangements can be used. A cabinet 48, which has drawers 50*a*, 50*b* and 50*c*, is attached to support column 44. Bed assembly A has bed support arms 22*d* and 22*e*, which are secured to and extend from support structure C.

Temperature is regulated in bed assembly A for the infant using a temperature sensor (not shown) and a thermostatic control 30*b* in control panel 30. Further details for making and using an infant heater are provided in the prior art, such as by U.S. Pat. No. 5,474,517, issued to Falk et al., and U.S. Pat. No. 5,980,449, issued to Benson et al., both of which are hereby incorporated by reference in their entirety for all purposes.

Figure 2:
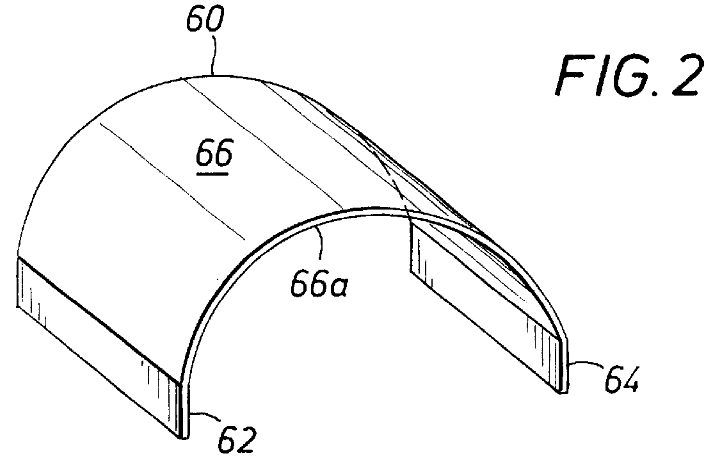
FIG. 2 is a perspective view of a light shield according to the present invention.

Turning to FIG. 2, a light shield 60 is illustrated according to the present invention. Light shield 60 is illustrative of one of many embodiments of a light shield according to the present invention. Light shield 60 has vertical support members 62 and 64 and a semi-circular structure 66 joined with vertical support members 62 and 64. A semi-circular member can be used without straight or vertical members. Semi-circular structure 66 has an inside surface 66*a*, which should be adequately spaced from an infant's head that is covered by the light shield. For example, the light shield should be adequately spaced to allow the infant to breathe properly.

A light shield according to the present invention can be made by heating and bending a sheet of plastic of a desired size to provide a lower surface that can rest on or in a bed assembly of an infant warmer or can be attached to the bed assembly of an infant warmer. The sheet of material is preferably substantially ductile and malleable. One can start with a rectangular sheet of material, possibly having a thickness ranging between about one-eighth of an inch to about one-half of an inch. The sheet of material can be bent and/or rolled so that it has an upper inside surface when placed in an orientation illustrated in FIGS. 1 or 2. With the sheet bent or rolled so as to have at least two lower contact surfaces capable of resting on a planar surface, an inside upper surface of the light shield should be between about five and about thirty inches above the planar surface, preferably between about ten and about twenty inches above the planar surface. The size and shape of the light shield should be adapted to accomplish the purposes outlined herein.

A light shield according to the present invention can be placed on or off of a bed assembly, depending on whether its use is desired at a particular time. Alternatively, the light shield can be secured to the bed assembly or to a different portion of the infant heater so as to block light from entering an infant s eyes or to support an opaque material that substantially blocks light from entering an infant's eyes. The infant heater and the light shield of the present invention operate to reduce undesired light stimulation to the eyes of an infant, particularly a premature baby having a very low birth weight and susceptible to distress caused by light entering the eyes. It is believed that the present invention provides a healthier and more soothing environment for a newborn baby that requires hospital care.

While the present invention has been shown and described in its preferred embodiment and in certain specific alternative embodiments, those skilled in the art will recognize from the foregoing discussion that various changes, modifications and variations may be made thereto without departing from the spirit and scope of the invention as set forth in the claims. Hence, the specific embodiments and any specific components and the like are merely illustrative and do not limit the scope of the invention or the claims herein.

What is claimed is:

1. An infant warmer, comprising:

an infant bed assembly adapted for supporting an infant, the bed assembly having a head end and a foot end;

a bed support holding and supporting the bed assembly;

a heat source adapted to provide heat for keeping an infant warm when the infant is placed on the bed assembly;

a support structure secured to the bed assembly or to the bed support and holding the heat source; and a light shield located on the head end of the bed assembly, wherein the light shield is adapted to cover the infant's head.

2. The infant warmer of claim 1, wherein the light shield is a rigid sheet of material formed to provide sufficient space between an upper surface of the bed assembly and the light shield to accommodate the infant's head.

3. The infant warmer of claim 2, wherein the light shield is adapted to removably rest on the bed assembly.

4. The infant warmer of claim 1, wherein the light shield is adapted to reduce the amount of light entering the infant's eyes.

5. The infant warmer of claim 4, wherein the light shield is opaque.

6. The infant warmer of claim 4, wherein the light shield is substantially transparent and is adapted to hold a sheet of fabric.

7. The infant warmer of claim 1, further comprising a light source secured to the support structure, wherein the light shield is located between the head end of the bed assembly and the light source so that light from the light source does not directly enter the infant's eyes, and wherein the light source provides light so that medical personnel can see the infant.

8. An infant warmer, comprising:

an infant bed assembly adapted for supporting an infant, the bed assembly having a head end and a foot end;

a bed support holding and supporting the bed assembly;

a heat source adapted to provide heat for keeping an infant warm when the infant is placed on the bed assembly;

a support structure secured to the bed assembly or to the bed support and holding the heat source;

a light shield located on the head end of the bed assembly; and a light source secured to the support structure, wherein the light shield is located between the head end of the bed assembly and the light source so that light from the light source does not directly enter the infant's eyes, and wherein the light source provides light so that medical personnel can see the infant.

9. The infant warmer of claim 8, wherein the bed assembly has a generally rectangular shape with perimeter edges and a length between the perimeter edge at the head end and the perimeter edge at the foot end, and wherein the light shield covers less than about 50 percent of the length.

10. A light shield adapted to rest on a bed assembly of an infant warmer, comprising:

a sheet of substantially rigid material;

the sheet having a lower support surface that is adapted to contact the bed assembly of the infant warmer and hold the sheet in a stable position;

the sheet having an inside upper surface that is adapted to cover and to be spaced from the head of an infant lying on an upper surface of the bed assembly, wherein the bed assembly has opposing first and second longitudinal sides; and the sheet is adapted to extend between the first and second longitudinal sides.

11. The light shield of claim 10, wherein the bed assembly has a length, and wherein the light shield is adapted to cover between about 10 and about 40 percent length.

12. The light shield of claim 11, wherein the sheet is substantially transparent plastic material capable of holding and supporting an opaque material.

13. The light shield of claim 10, wherein the light shield consists only of the sheet of substantially rigid material and one or more members for adapting the light shield to rest on the bed assembly.

14. The light shield of claim 10, wherein the light shield consists only of the sheet of substantially rigid material and wherein the sheet of substantially rigid material has edges and is bent or curved so that the edges comprise the lower support surface.

* * * * *

UNITED STATES PATENT AND TRADEMARK OFFICE

CERTIFICATE OF CORRECTION

PATENT NO. : 6,413,205 B1
DATED : July 2, 2002
INVENTOR(S) : Rosamma K. Finny

It is certified that error appears in the above-identified patent and that said Letters Patent is hereby corrected as shown below:

Column 4,
Line 27, "infant s" should read as -- infant's --.

Column 6,
Line 16, "percent length" should read as -- percent of the length --.

Signed and Sealed this

Seventeenth Day of September, 2002

*Attest:*

JAMES E. ROGAN

*Attesting Officer*

*Director of the United States Patent and Trademark Office*